United States Patent [19]
Borella et al.

US005510114A

[11] Patent Number: 5,510,114
[45] Date of Patent: Apr. 23, 1996

[54] SLOW RELEASE PHARMACEUTICAL COMPOSITION CONTAINING A BILE ACID AS AN ACTIVE INGREDIENT

[75] Inventors: Fabio Borella, Milan; Alberto Brandt, Rome; Fabio Carli, Trieste, all of Italy

[73] Assignee: Instituto Biochimico Italiano Giovanni Lorenzini S.p.A., Milan, Italy

[21] Appl. No.: 236,986

[22] Filed: May 2, 1994

[30] Foreign Application Priority Data

May 18, 1993 [IT] Italy .................. MI93A1014

[51] Int. Cl.⁶ .................. A61K 9/22; A61K 9/58; A61K 9/62; A61K 35/413
[52] U.S. Cl. .................. 424/452; 424/457; 424/458; 424/461; 424/462; 424/465; 424/468; 424/494; 424/497; 424/528; 514/769; 514/781; 514/782; 514/783; 514/877; 514/774; 514/779; 514/772.3
[58] Field of Search .................. 424/456, 457, 424/458, 459, 461, 462, 468, 469, 470, 494, 497, 496; 514/877

[56] References Cited

U.S. PATENT DOCUMENTS

| | | | |
|---|---|---|---|
| 2,918,411 | 12/1959 | Hill | 167/82 |
| 4,572,833 | 2/1986 | Pedersen et al. | 424/20 |
| 5,262,172 | 11/1993 | Sipos | 424/490 |

FOREIGN PATENT DOCUMENTS

| | | |
|---|---|---|
| 0524395 | 1/1993 | European Pat. Off. . |
| 0526862 | 2/1993 | European Pat. Off. . |
| 2036558 | 7/1980 | United Kingdom . |

Primary Examiner—Thurman K. Page
Assistant Examiner—James M. Spear
Attorney, Agent, or Firm—Hedman, Gibson & Costigan

[57] ABSTRACT

A slow-release pharmaceutical composition containing a bile acid as active ingredient and comprising at least one bioadhesive substance and at least one high specific gravity substance, an aliquot thereof being enteric coated and the remainder being non-enteric coated.

8 Claims, No Drawings

SLOW RELEASE PHARMACEUTICAL COMPOSITION CONTAINING A BILE ACID AS AN ACTIVE INGREDIENT

PRIOR ART

Slow-release pharmaceutical compositions for oral administration are amply documented in scientific and patent literature.

For example, U.S. Pat. No. 2,918.411 discloses a pharmaceutical composition For oral administration essentially comprising a multiplicity of minute pellets consisting of (a) polyvinylpyrrolidone, (b) a water soluble agent melting at 45° C. min. and selected among saturated fatty acids, esters of saturated fatty acids of mono-, di-, and trihydric alcohols, mono- and polyesters of saturated fatty acids, saturated aliphatic ketones, and pharmaceutically acceptable sterols, and (c) a drug.

U.S. Pat. No. 4,572,833 discloses a controlled release pharmaceutical composition for oral administration wherein potassium chloride microgranules are coated with a membrane comprising a solvent, a film-forming substance dissolved in said solvent, and a hydrophobic substance microdispersed in said film-forming mixture.

The use of bile acids for humans' cholesterol-oversaturated lithogenous bile desaturation and biliary calculi lysis is well known. Among them, particularly preferred are the chenodeoxycholic, ursodeoxycholic and tauroursodeoxycholic acids.

However, to bring about the desired beneficial effects, the therapy based on said acids requires regular, long-lasting treatments (from 6 months to 2 years).

This is one reason why efforts have been made to secure the patient's compliance, who, being often asymptomatic, does not feel inclined regularly to take medicines.

On the basis of the results obtained from clinical trials, ursodeoxycholic acid was in several cases administered at a single evening dose instead of multiple doses, the daily dose being 10 mg/kg/of body weight.

However, said single evening dose, undoubtedly more practical, must be enough to secure antilithogenous protection for the whole day. Calculi formation, if any, especially takes place during the periods of fasting within the span of the day, i.e. during night-time and during the hours preceding lunch.

This is another reason supporting administration in the evening. Slow release pharmaceutical formulations based on ursodeoxycholic acid are already available.

For example, Lehner's U.S. Pat. No. 4,263,272 discloses and claims a composition that may be provided in two pharmaceutical forms, i.e.:

a) a solid unit dosage form comprising tablets or pills made up from several concentric layers.

In a typical embodiment, said solid unit dosage form consists of:

a core obtained by compression and containing a bile acid, starch, microgranular cellulose, formaldehyde, casein, and Mg stearate;

a first coating layer consisting of Eudragit®, which is an methacrylic acid copolymer;

a second coating layer consisting of a bile acid, polyvinylpyrrolidone, polyethylene glycol, starch and carboxymethylcellulose;

an external layer consisting of Eudragit®, which is an methacrylic acid copolymer talc, titanium dioxide, colouring agent, alumina and polyethylene glycol;

b) a divided unit dosage form consisting of gelatin capsules containing microencapsulated bile acid granules.

Bile acid granules are coated individually with gelatin. The drug is thus microencapsulated in gelatin coacervates which are subsequently hardened to a different degree and in a different amount with formaldehyde to obtain a different degree of gelatin hydrolysis. European patent appln. No. EP-A-529395 filed on May 18, 1992, by Boniscontro and Gazzone S.r.l., discloses a delayed release system based on gelling substances, in particular mixtures of sodium and calcium alginates, capable of progressively liberating the active ingredient by diffusion through the gel.

More recent studies of bile acids absorption provided evidence of their being absorbed to a very different extent in the various areas of the gastrointestinal tract.

Chenodeoxycholic and ursodeoxycholic acids absorption and, consequently, bioavailability are directly affected by the solubility of same in the stomach and in the intestine. Said acids are very little soluble in the stomach, the pH being acid, and leave the stomach according to natural stomach emptying mechanisms. If administered on an empty stomach, they pass into the duodenum in approx. 1 hr. They dissolve in the intestine and particularly in the small intestine, where the most marked absorption takes place.

In spite of such a wealth of information, the compositions containing bile acids that are already known exhibit a bioavailability and kinetics of release inadequate for the treatment of biliary lithiasis. Therefore, the need for compositions of improved characteristics, capable of overcoming the disadvantages of the compositions of the prior art is deeply felt.

SUMMARY

The present invention relates to a composition containing a bile acid as active ingredient suitable for a single daily administration, which represents an unexpected improvement over the slow-release compositions known to the prior art.

The composition of the present invention contains a bile acid as active ingredient and comprises at least one bioadhesive substance and at least one high specific gravity substance, may be provided in the form of 0.5–2 mm dia. coated particles or of tablets, and is characterized by having an aliquot enteric coated with gastroresistant substances and the remainder non-enteric coated. Said composition shows a slow release of the bile acid, long residence times in the stomach and in the intestine, a high bile acid bioavailability, and is particularly suitable for a preset bile acid release in the various segments of the gastrointestinal tract.

DETAILED DESCRIPTION OF THE INVENTION

The characteristics and advantages of the slow-release pharmaceutical compositions containing a bile acid as an active ingredient according to the present invention will be apparent from the detailed description that follows.

Said compositions comprise at least one bioadhesive substance and at least one high specific gravity substance and have an aliquot enteric coated with gastroresistant substances and the remainder non-enteric coated.

In addition to the above constituents, the present compositions may contain excipients, binders, lubricants, and other substances commonly used in pharmaceutical formulations.

Preferred bile acids are the chenodeoxycholic, ursodeoxycholic, and tauroursodeoxycholic acids.

Preferred bioadhesive substances for use in the present composition are sodium carboxymethylcellulose, hydroxypropyl cellulose, hydroxypropyl methylcellulose, sodium alginate and the corresponding acid, tragacanth gum, guar gum, arabic gum, gelatin, pectin, scleroglucan, schizophyllane, xanthan gum, chitosan, linear polymers of acrylic acid and salts thereof.

Preferred high specific gravity substances are barium sulphate, powdered metallic iron, samarium oxide, erbium oxide, magnesium trisilicate, aluminium trisilicate, magnesium aluminium trisilicate, titanium dioxide.

Gastroresistant substances include cellulose derivatives, such as cellulose triacetate, cellulose acetate butyrate, cellulose acetate phthalate, cellulose acetate trimellitate, and acrylic derivatives available under the trademark of Eudragit L® which is an methacrylic acid copolymer, Type C as disclosed in USPXXII or Eudragit S® which is an methacrylic acid copolymer, Type B as disclosed in USPXXII.

The compositions are preferably prepared in the form of coated particles, 0.5 to 2 mm in diameter, to be packed into capsules suitable for a single daily administration.

The method of production consists of the following steps:

a) preparing a powder mixture comprising the bile acid, the bioadhesive substance, and the high specific gravity substance;

b) transforming said powder mixture into granules forming the cope to be coated;

c) coating an aliquot of said granules (of point b) with a gastroresistant and bioadhesive film, capable of delaying bile acid release;

d) coating the remainder of said granules (of point b) with a bioadhesive not gastroresistant film, capable of delaying bile acid release;

e) preparing the final composition to be packed into capsules by mixing the granules of step c) with the granules of step d).

Therefore, in the present embodiment, the bile acid and the high specific gravity substance are present in the core, the bioadhesive substance is present in the core and in the coating layer, and the gastroresistant substance is present in the coating layer of an aliquot of granules.

The aliquot of enteric coated granules (of step c) is 40 to 60% by wt. of the final composition.

The powder mixture used in step a) consists of:

bile acid, 10 to 90% by bioadhesive substance, 1 to 15% by wt.

high specific gravity substance, 5 to 40% by wt.

other substances of common usage in pharmaceutical practice, such as cellulose, polyvinylpyrrolidone, etc., balance to 100.

The transformation of said powder mixture into granules is carried out according to known techniques, such as extrusion followed by spheronizing and sieving, or granulation in a rotary drum granulator followed by sieving.

Granules of steps c) and d) are coated by known techniques by spraying with a film-forming suspension or solution, for example in a fluid bed or in a basin.

A film-forming suspension capable of producing a gastroresistant film for step c) consists, e.g., of Eudragit L®, triacetin, talc, and water in such amounts that the resulting coating layer has the following composition: 50 to 90% by wt. Eudragit L®, which is an methacrylic acid copolymer, Type C as disclosed in USPXXII 5 to 10% by wt. triacetin, and 5 to 20% by wt. talc.

A film-forming suspension capable of producing a not gastroresistant film for step d) consists, e.g., of hydroxypropyl methylcellulose, Carbomer® which is polycarbophil (polyacrylic acid) and dibutyl phthalate in methylene chloride-ethanol solvent in such amounts that the resulting coating layer has the following composition: 10 to 50% by wt. hydroxypropyl methylcellulose, 30 to 90% by wt. Carbomer® which is polycarbophil (polyacrylic acid) and 5 to 10% by wt. dibutyl phthalate.

The film applied to the granules is 4 to 7% by wt. of the final composition.

The compositions of the present invention may be prepared not only in the form of granules to be packed into capsules, but also in the form of tablets.

The compositions of the present invention exhibit high residence times in the stomach and in the intestinal tract, a slow release of the bile acid and a high bioavailability of same. Therefore, they are particularly suitable for a controlled release of the drug in the gastrointestinal tract comprising stomach, jejunum and ileum. Said characteristics make them suitable for dosage unit forms, i.e. capsules or tablets, to be administered per os once a day to prevent and treat biliary calculi in man.

The following examples, which are given by way of illustration and not of limitation, refer to compositions wherein the bile acid is ursodeoxycholic acid. Other bile acids may be used without departing from the scope of this invention.

EXAMPLE 1

1a) A powder mixture having the following composition was prepared: 73.2% by wt. UDCA (ursodeoxycholic acid), 2.9% by wt. xanthan gum, 9.8% by wt. barium sulphate, 8.4% by wt. microcrystalline cellulose, 4.7% by wt. PVP CL.

1b) Said mixture was extruded through a twin screw extruder, after moistening the mass within the plant with demineralized water. Extrusion was carried out by forcing the damp mixture through a die with 1 mm dia. orifices.

The operating parameters are as follows:

powder flow rate: 58 g/min water flow rate: 15 g/min screw rotation: 170 rpm die max. temperature: 50° C.

The extruded filaments were processed in a spheronizer set to 1000 rpm for a period of 10 min. The resulting spheroids were dried in a fluid bed under a stream of air heated to 70° C. Once drying had been completed, the product was discharged, sieved mechanically to provide the fraction sized 0.800–1.180 mm.

1c) Pellets (300 g) obtained in step 1b) were suspended in heated air stream in a fluid bed apparatus for film coating and coated with a polymeric membrane obtained by spraying the following film-forming suspension: 15% by wt. Eudragit L® 100-55, which is an methacrylic acid copolymer, Type C as disclosed in USPXXII 1.5% by wt. triacetin, 1.5% by wt. talc, 82% by wt. demineralized water.

The operating conditions were as follows:

spray nozzle: 1 mm spraying pressure: 1 bar film-forming suspension feed rate: 3–5 g/min air rate: 5 m/s inlet-air temperature: 45°–50° C.

product temperature: 32° C.

The polymer amount of the coating film was 5% by wt. of the pellet weight.

1d) Pellets (500 g) obtained in step 1b) were suspended in heated air stream in a fluid bed apparatus for Film coating and coated with a polymeric membrane obtained by spraying the following film-forming suspension: 1.9% by wt. 15 cps hydroxypropyl methylcellulose, by wt. Carbomer®, which is polycarbophil 0.6by wt. dibutyl phthalate 74.3% by wt. methylene chloride, 18.6% by wt. U.F. grade ethanol.

The operating conditions were as follows:

spray nozzle: 1 mm spraying pressure: 1 bar film-forming suspension feed rate: 4.5 g/min air rate: 5 m/s inlet-air temperature: 40°–42° C.

outlet-air temperature: 35°–36° C.

product temperature: 36°–38° C.

The polymer amount of the coating film was 6% by wt. of the pellet weight.

1e) The final composition was obtained by mixing pellets prepared according to step 1c) with pellets prepared according to step 1d) in equal by wt. amounts.

The dissolution rate of said final composition was determined as described in U.S.P. XXII (paddle method, 100 rpm, phosphate buffer (900 ml), pH 7.5, composition: 200 mg UDCA equivalents).

The results obtained are shown in Table 1.

TABLE 1

| UDCA dissolution rate from the composition under step 1e | |
|---|---|
| Time (h) | Dissolved fraction (%) |
| 1 | 28 |
| 2 | 44 |
| 3 | 49 |
| 4 | 55 |
| 6 | 62 |
| 8 | 75 |
| 10 | 80 |
| 24 | 90 |

EXAMPLE 2

2a) A powder mixture having the following composition was prepared: 70.5% by wt. UDCA, 5% by wt. xanthan gum, 10% by wt. barium sulphate, 14.5% by wt. microcrystalline cellulose.

2b) Said mixture (800 g) was fed to a rotary drum granulator and sprayed with 10% solution of PVP K 25 in demineralized water (760 g of solution). Once wet granulation had been completed, the granules were dried.

The operating parameters of the process (wet pelletizing phase) were as follows:

spray nozzle: 1 mm spraying pressure: 0.5–1 bar inlet-air temperature: 22°–25° C.

outlet-air temperature: 20°–22° C.

outlet-liquid rate: 80–100 g/min drum rotation speed: 500–1000 rpm

Drying was carried out at the following operating conditions:

inlet-air temperature: 80° C.

outlet-air temperature (cycle end): 50° C.

drum rotation speed: 1500 rpm.

Once the cycle had been completed, the product was sieved to provide the fraction sized 0.800–1.180 mm.

2c) Granules (500 g) obtained in step 2b) were suspended in heated air stream in a fluid bed apparatus for film coating and coated with a polymeric membrane obtained by spraying the following film-forming suspension: 15% by wt. Eudragit L® 100-55, 1.5% by wt. triacetin, 1.5% by wt. talc, 82% by wt. demineralized water.

The operating conditions were as follows:

spray nozzle: 1 mm spraying pressure: 1 bar film-forming suspension feed rate: 3–5 g/rain air rate: 5 m/s inlet-air temperature: 45°–50° C.

product temperature: 32° C.

The polymer amount of the coating Film was 5% by wt. of the granule weight.

2d) Granules (500 g) obtained in step 2b) were suspended in heated air stream in a fluid bed apparatus for film coating and coated with a polymeric membrane obtained by spraying the following film-forming suspension: 0.6% by wt. ethylcellulose (from aqueous dispersion), 0.6% by wt. xanthan gum, 0.2% by wt. dibutyl phthalate, 98.6% by wt. demineralized water.

The operating conditions were as follows:

spray nozzle: 1 mm spraying pressure: 1.4 bar film-forming suspension Feed rate: 4–6 g/min air rate: 3 m/s inlet-air temperature: 66°–68° C.

product temperature: 38°–40° C.

The polymer amount of the coating film was 6% by wt. of the granule weight.

2e) The final composition was obtained by mixing granules prepared according to step 2c) with granules prepared according to step 2d) in equal by wt. amounts.

The dissolution rate of said composition was determined as described in U.S.P. XXII (paddle method, 100 rpm, phosphate buffer (900 ml), pH 7.5, composition: 200 mg UDCA equivalents).

The results obtained are shown in Table 2.

TABLE 2

| UDCA dissolution rate from the composition under step 2e | |
|---|---|
| Time (h) | Dissolved fraction (%) |
| 1 | 18 |
| 2 | 38 |
| 3 | 59 |
| 4 | 75 |
| 6 | 80 |
| 8 | 84 |
| 10 | 88 |
| 24 | 98 |

Comparative in vivo tests of the composition as per Example 1 and of the product disclosed in Lehner's patent mentioned hereinbefore (trademark: Deursil RR®) brand of ursodeoxycholic acid were conducted using healthy volunteers, administered a single evening dose per os.

The composition of the present invention showed an improved UDCA bioavailability and kinetics of release.

We claim:

1. Slow release pharmaceutical composition containing a bile acid as active ingredient and provided in the form of 0.5–2 mm diameter coated particles suitable to be manufactured in the form of capsules or tablets, wherein the core of said particles consists of 10 to 90% by weight of a bile acid, 1 to 15% by weight of a bioadhesive substance, 5 to 40% by weight of a high specific gravity substance selected from the group consisting of barium sulfate, powdered metallic iron, samarium oxide, erbium oxide, magnesium trisilicate, aluminum trisilicate and titanium dioxide, the balance to 100 being constituted by cellulose or polyvinylpyrrolidone, an aliquot of 40 to 60% by weight of said particles being enteric coated with gastroresistant substances and the remainder being coated with a non-enteric coating.

2. The composition according to claim 1, wherein said bioadhesive substance is selected from the group consisting of sodium carboxymethylcellulose, sodium alginate and the corresponding acid, tragacanth gum, guar gum, arabic gum, gelatin, pectin, scleroglucan, schizophyllane, xanthan gum and chitosan.

3. The composition of claim 1, wherein said gastroresistant substances are selected from the group consisting of cellulose triacetate, cellulose acetate, cellulose acetate trimellitate, methacrylic acid copolymer, Type C-USP/NF XXII and methacrylic acid copolymer, Type B-USP/NF XXII.

4. The pharmaceutical composition according to claim 1, wherein the coating layer of said enteric coated particles consist of 50 to 90% by weight of methacrylic acid copolymer, Type C-USP/NF XXII, 5 to 10% by weight of triacetin, and 5 to 20% by weight of talc.

5. The pharmaceutical composition according to claim 1, wherein the coating layer of said non-enteric coated particles consists of 10 to 50% by weight hydroxypropyl methylcellulose, 30 to 90% by weight of polycarbophil and 5 to 10% by weight of dibutyl phthalate.

6. The pharmaceutical composition according to claim 1, wherein said coating layer of said particles is 4 to 7% by weight of said composition.

7. The pharmaceutical composition according to claim 1, wherein said bile acid is selected from the group consisting of ursodeoxycholic, chenodeoxycholic and tauroursodeoxycholic acids.

8. The pharmaceutical composition according to claim 1, being in the form of capsules or tablets containing a bile acid dose suitable for a single daily administration.

* * * * *